United States Patent
Marovets (10) Patent No.: US 9,737,237 B2
(45) Date of Patent: Aug. 22, 2017

(54) SYSTEM, METHOD AND APPARATUS FOR DETERMINING THE THICKNESS OF ORTHOTICS NEEDED TO CORRECT FOR DIFFERENCES IN LEG LENGTH

(71) Applicant: Jack L. Marovets, Cedar Rapids, IA (US)

(72) Inventor: Jack L. Marovets, Cedar Rapids, IA (US)

( * ) Notice: Subject to any disclaimer, the term of this patent is extended or adjusted under 35 U.S.C. 154(b) by 315 days.

(21) Appl. No.: 13/733,722

(22) Filed: Jan. 3, 2013

(65) Prior Publication Data

US 2013/0172787 A1 Jul. 4, 2013

Related U.S. Application Data

(60) Provisional application No. 61/631,368, filed on Jan. 3, 2012.

(51) Int. Cl.
*A61B 5/107* (2006.01)
*A61B 5/103* (2006.01)
*G01G 19/50* (2006.01)

(52) U.S. Cl.
CPC .......... *A61B 5/1072* (2013.01); *A61B 5/1036* (2013.01); *G01G 19/50* (2013.01)

(58) Field of Classification Search
CPC ..... A61B 5/1036; A61B 5/107; A61B 5/1072; A61B 5/4504; G01G 19/44
USPC ............ 600/587, 592, 595; 177/1, 2, 3, 199, 177/200, 245, 25.11–25.14; 33/515; 73/172
See application file for complete search history.

(56) References Cited

U.S. PATENT DOCUMENTS

| | | | | | |
|---|---|---|---|---|---|
| 4,014,398 | A | * | 3/1977 | Gresko | 600/592 |
| 5,088,504 | A | * | 2/1992 | Benesh et al. | 600/594 |
| 5,285,022 | A | * | 2/1994 | Antone | 177/253 |
| 5,790,256 | A | * | 8/1998 | Brown et al. | 356/613 |
| 5,823,974 | A | * | 10/1998 | Grassi | 600/595 |
| 6,437,257 | B1 | * | 8/2002 | Yoshida | 177/199 |
| 6,962,568 | B1 | * | 11/2005 | Morger | 600/595 |
| 2004/0238234 | A1 | * | 12/2004 | Blumentritt et al. | 177/177 |
| 2005/0119592 | A1 | * | 6/2005 | Frank | A61B 5/1036 600/594 |
| 2005/0183894 | A1 | * | 8/2005 | Lair | 177/3 |

FOREIGN PATENT DOCUMENTS

FR 2491754 A * 4/1982

OTHER PUBLICATIONS

Machine Translation FR 2491754.*

* cited by examiner

*Primary Examiner* — David J McCrosky
(74) *Attorney, Agent, or Firm* — Goodhue, Coleman & Owens, P.C.

(57) ABSTRACT

The present invention is a system, method, and apparatus that relates to providing a quick measurement the difference, if any, of a person's left and right leg lengths, in order to determine the correct thickness of an orthotic insert for the left and/or right shoes in order to provide correction and alignment of a person's skeletal frame.

3 Claims, 5 Drawing Sheets

SYSTEM, METHOD AND APPARATUS FOR DETERMINING THE THICKNESS OF ORTHOTICS NEEDED TO CORRECT FOR DIFFERENCES IN LEG LENGTH

CROSS-REFERENCE TO RELATED APPLICATIONS

This application claims priority to and is a conversion of: U.S. Provisional Patent Application Ser. No. 61/631,368, entitled System, Method, And Apparatus For Determining The Thickness Of Orthotics To Correct For Differences In Leg Length, which is herein incorporated in its entirety by reference.

FIELD OF THE INVENTION

The present invention is a system, method, and apparatus that relates to providing a quick measurement the difference, if any, of a person's left and right leg lengths, in order to determine the correct thickness of an orthotic insert for the left and/or right shoes in order to provide correction and alignment of a person's skeletal frame.

BACKGROUND OF THE ART

There are several macro and market specific trends contribute to the growth of the global orthopedic industry. Macro demographic factors continue to drive growth in the overall industry, which, in turn are boosting demand for ancillary/adjunctive/conjunctive devices. The orthopedic orthotics market, consisting of ancillary devices used post-operatively as well as for non-operative functions, is being bolstered by the growth in the parent orthopedic industry.

The United States, Europe and Japan account for a lion's share of the orthopedic orthotics market, according to various market research reports. Changing consumer profile, together with rising disposable incomes, expanded coverage of health insurance and public health programs world over, dictates healthy growth for the worldwide orthopedic orthotics industry. Increasingly active lifestyles of people, and rising occurrence of vascular diseases due to obesity are driving growth in the orthopedic orthotics market. On the other hand, the global economic meltdown, increasing availability of pain medications, continuous developments and improvements in invasive procedures are likely to restrict the extent of growth.

Value-added functionalities, along with technically advanced materials, are triggering higher use of orthopedic support devices. The market consists of a variety of products ranging from those that meet highly specific clinical needs to inexpensive over-the-counter devices. Revolutionary improvements in the material and modeling technologies have eased the task of customizing and/or standardizing specifications of orthotic devices, extended the lifespan of products, enhanced the pliability or rigidity of braces in accordance with consumer needs. The US constitutes the largest market for orthopedic braces. Repetitive stress injuries and increasing number of implant surgeries are primed to boost sales of orthotic braces geared for these implications. Growing incidence of injuries as a result of an active aging population is one of the major factors spurring non-operative use of orthopedic braces and supports.

One of the key characteristics of the orthotics market segment is consistent demand stemming from recurrent replacement and modification of products. An average orthotic device lasts for one to three years, and needs to be replaced on a periodic basis, thus ensuring continuous demand for orthotic devices. Currently, orthotic devices are being made more durable, effective and lightweight through advanced graphite and carbon fiber materials. Moreover, products are turning more sports-specific with specialized devices for individual sports.

Dr. Scholl's company is a good illustration of the existing art, and the deficiencies in the existing art as related to orthotics. Dr. Scholl's has a line of custom fit orthotics that are sold at self-serve kiosks. The kiosk is designed with thousands of sensors that are used to identify where a person puts the most pressure on their feet. Their FootMap Analysis appears on the screen highlighting a person's specific pressure point. Red coloration indicates high pressure, and other intermediate colors indicate medium pressure, and blue coloration indicates areas of low pressure.

Based on the kiosk's sophisticated measurements, a "packaged match pair" of Dr. Scholl's Custom Fit Orthotic Inserts are recommended in order to provide a person customized support by putting a person's feet into more supported positions and disperse pressure levels evenly across both feet. Even though Dr. Scholl's has developed a very sophisticated kiosk that is capable of measuring differences in pressures between the left foot and right foot with regard to arches, heels, etc., there are no measurements taken to determine a difference in leg length, which a significant percentage of the general population is affected with. Therefore, the orthotics do not take into account a difference in leg length, and a basic problem is not solved. The fact that Dr. Scholl does not believe this problem is significant is they sell orthotics in matched sets. Following are pages from Dr. Scholl's website about their kiosk:

Disparities in leg length, in fact, may be relatively common: a study published in Spine in 1983 found that 43.5 percent of people with no back pain symptoms had leg-length inequality of five millimeters or more, while a whopping 75.4 percent of study subjects with chronic low-back pain had similar leg-length discrepancies.

"Leg-length inequality is a significant factor in chronic low-back pain. But it's associated not only with lumbar spine pain but hip joint pain, as well," says Leo Bronston, DC, who practices in La Crosse, Wis., and serves as vice president of the ACA's Council on Orthopedics. "It can also affect the knee, but most of the time you're going to find that a patient will have chronic lower-back pain and hip pain."

In the hip area, the leg that is longer carries more weight, making it vulnerable to abuse in weight-bearing activities like walking or running. "Long-standing leg-length inequality has been shown to lead to hip joint arthritis. There are some studies on that, but they aren't indexed studies," says Dr. Bronston.

Despite its apparent prevalence, leg-length inequality is all too often overlooked in diagnosing chronic back and hip pain. "Experts in the field will tell you that anyone suffering from chronic back, hip, knee, or leg pain should be evaluated for leg-length inequality," Dr. Bronston says. "It should be a standard rule out."

When one leg is shorter than the other, you may be dealing with either a functional leg-length discrepancy, which can often be completely corrected by manipulation, or an anatomical leg-length discrepancy, which is a permanent leg-length deficit.

Functional discrepancies, explains Dr. Bronston, have a variety of causes. "You can have muscle spasms in one hip; you can have hip capsule tightness; you can have adductor muscle spasm on one side; and you can have pronation of one foot and supination of the other foot. Those are the main sources of a functional disparity," he says.

"Anatomical discrepancies also stem from a variety of sources," says Henry West, DC, an ACA state delegate representing Idaho. "There can be a difference in the length of the femur or the tibia, for example. Also, if the patient has had knee surgeries or ankle injuries or fractures, that can lead to leg-length discrepancies." Polio and other disease processes, says Dr. Bronston, can also render one leg shorter than the other.

The effects of leg-length discrepancies, Dr. West says, can often be seen in the quirks of an athlete's performance. "My father used to treat a lot of the baseball players for the Class D Pocatello Cardinals, and was very good friends with the coach," he recalls. "If a right-handed ballplayer was consistently hitting pop flies, often we'd find that his right leg would be short-so when he'd swing, he'd be undercutting. If his left leg was too short, he'd be hitting ground balls because he was overcutting." Much the same thing happens in other sports, like basketball and golf. "If your right leg is short and you tend to shoot off the right leg, even though you're a jump shooter, you'll fall short and hit the rim instead of putting it through the hoop," Dr. West says. "If you're a golfer, you're not going to hit the ball where you're aiming it because of a shift of the pelvis, which may relate to a functional or an anatomical short leg."

Many of us may have these leg-length disparities and never notice them, like the study subjects in the Spine article who had no low-back pain. "It's clinically significant when you have symptoms," says Dr. West, and at that point, the DC must determine the extent of the leg-length discrepancy and its origins. This involves a combination of clinical and radiographic examination. "The mainstay is the clinical examination; that's going to give you most of the information. A radiographic exam will confirm a leg-length deficiency when clinically correlated," Dr. Bronston adds.

To assess an actual, rather than a functional, leg length disparity, the chiropractor should measure from a landmark on the pelvis—usually the anterior superior iliac spine—out to the medial maleolus, and then compare each side. Dr. West advises placing the patient on a high-low table, without shoes, for this measurement. "Experts will tell you that an eighth of an inch to a quarter inch could be a physiological 'normal,'" Dr. Bronston says. "There can be some variables, including examiner error or the technique of the measuring. But anything over about 3/16 of an inch, or five millimeters, is clinically significant, and it can definitely affect the outcomes of your patient's pain."

"In many cases, your patients may be already aware of the problem. Many times you can adjust the patient and it takes care of itself, maybe with just a shift of a sacroiliac joint, but if it's not holding, you need to look at a heel lift or an orthotic shoe."

In some patients, particularly the elderly, hip and knee replacements can lead to anatomical leg-length discrepancies. "We see a lot more patients today who've had knee and hip replacements, and the majority of them do present with leg-length inequality that sometimes is the source of their chronic low-back pain," says Dr. Bronston. "The joint is replaced and the hip and knee pain goes away, but then the patient may start presenting with low-back pain due to inequality in the limbs because of the replacement. Although surgeons try to make sure the leg with the replacement is of the same length as the other, there's no guarantee. After surgery, muscular imbalances can change, so follow-up with these patients is important."

Treatment of chronic low-back pain or knee pain that stems at least in part from leg-length inequality is a two-step process, Dr. Bronston says. "The first consideration is spinal manipulation to reduce the misalignments and muscular tightness within the lower back and pelvis, which are normal occurrences with leg-length inequality. The second would be utilization of a heel lift under the short-leg side to stabilize and level the pelvis. A lift gives the spine a more level foundation on which to rest, reduces stress on spinal joints and distortions of the vertebrae, and normalizes muscular balance." In fact, he believes that 75 percent of patients with low-back pain would find their symptoms normalized by this process. "Hip pain treatment would use the same two-step process, although I would work more on the musculature of the pelvis and hip using some direct exercises of flexibility, either passive or active, in order to increase some of the flexibility of the hip joint. That would be the only difference."

Heel lifts may not be necessary for the patient with a functional leg-length inequality, which can in many cases be remedied fully by manipulation. "But if there's an anatomical inequality, there are going to be recurrent problems without a shoe lift or a shoe correction," Dr. West says. "Probably two to four times a week in my practice alone, I'll have a patient say, 'I had no idea that was causing so much of a problem! I feel so much better since you put that lift in.'" Heel lifts don't have to completely correct the discrepancy in order to achieve these results. "Let's say there's a half-inch deficiency in a standing x-ray of the right femoral head, as compared to the left femoral head," Dr. West says. "When creating the lift, make it one-half to maybe two-thirds of the difference, and it works out fine." Dr. Bronston agrees, and both note that extreme discrepancies will require a lift in the sole, as well as the heel. "If the leg-length difference is greater than a half inch, then you have to build the sole up, as well. For some patients, you may have to not just provide a heel lift, but also have a cobbler add to the sole so they're not tripping over their toes," Dr. Bronston says.

Although the heel lift corrects the problem, chiropractic manipulation will speed the recovery process. "You can just assume that these patients will be treated with manipulative therapy for the nominate distortion pattern, electrical stimulation for the muscle rehabilitation, and ultrasound," Dr. West says. "And they get over their pain much faster with this combination of treatment and therapies than just with the heel lift alone. But then they continue with the heel lift as a correction."

Some patients are recalcitrant about permanently adding lifts to their footwear wardrobe. "I wear glasses. I wish I didn't have to, but it's sure better than the alternative," Dr. West says. "A lot of people only want to wear a heel lift a month or two to get relief, but it doesn't work that way. You need to keep wearing it. When you forget the heel lift, or your corrective shoe, then you're more likely to get symptoms back. After two or three recurrences, people usually learn."

"We walk on the foundation of our feet. We're not suspended by sky hooks," Dr. West comments. "Doctors of chiropractic should realize that leg length is very important as it relates to the balance of the pelvis and the structural stress that is a consequence of leg-length inequality." For additional background information, see various attachments to this provisional patent.

While there are dozens of devices for correcting deficiencies in a person's feet, which cause misalignment of ankles, knees, and hips, which can lead to pain in these joints, or pain in the back, shoulders, and neck of a person whose legs are of a different length, and although it is a well-recognized problem, there is no quick, inexpensive, method of determining difference in leg lengths, in order to provide an orthotic of the correct thickness for the left foot and/or right foot to compensate for the difference, and to alleviate the myriad of problems this common problem causes. Therefore, there is an unmet need to solve this problem.

OBJECTS AND FEATURES OF THE INVENTION

It is an object of the present invention to provide a system, method, and apparatus for a marketing system that quickly determines the difference, if any, in the length of a person's legs in order to provide the inserts of the proper thickness to correct for any difference in leg length.

SUMMARY OF THE INVENTION

The present invention provides a variety of methods for quickly ascertaining the difference, if any, between a person's left and right leg lengths. The resulting measurements can be used to correctly determine the thickness of an insert for the left and/or right shoes in order to provide correction and alignment of a person's skeletal frame, and relief from pain, and possibly avoiding surgery, such as knee and/or hip replacement(s).

DETAILED DESCRIPTION OF VARIOUS EMBODIMENTS

Figure 1:
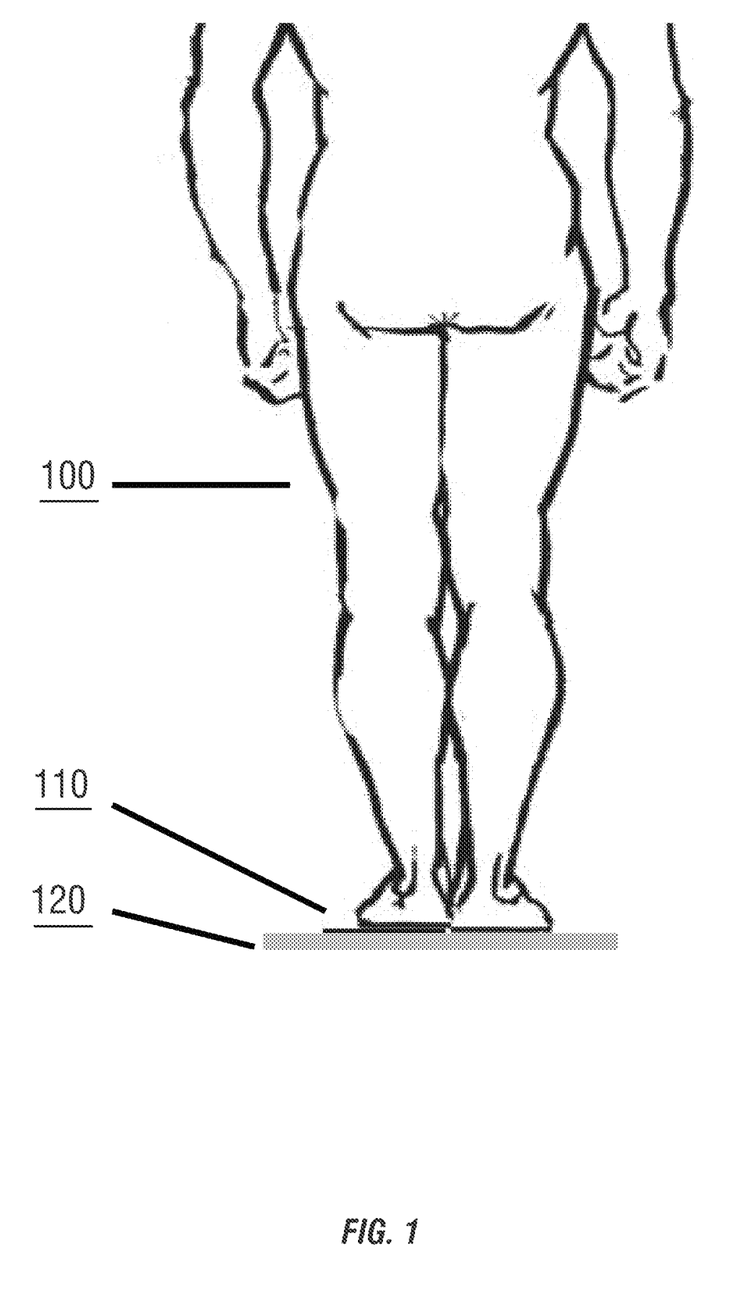
FIG. 1 is an illustration of the present invention.

The preferred embodiment of the present invention is illustrated in FIG. 1 in its simplest form, which consists of the following elements:

Person 100 is illustrated with unequal length legs. The left leg is illustrated as shorter than the right leg.

Elevation Shim 110 is illustrated placed between Person 100's left leg and floor platform 120 to make up the difference in Person 100's leg length. Elevation Shim 110 is one of various thicknesses that could be made available at an Orthotic Kiosk, at a Podiatrist's Office, at an Orthotics Store, or shipped via a package to a potential customer's house or place of business for use in self-measurement in their own private setting. The various thicknesses of Elevation Shim 110s are required to be able to determine a range of difference in Person 100's leg length. As an example, a standard package of Elevation Shim 110s could include the following thicknesses for Person 100 to determine the correct thickness for either the left or right orthotic that is needed to equalize the difference in their leg length: 1 mm, 2 mm, 3 mm, 4 mm, 5 mm. Elevation Shim 110's are a simple means for Person 100 to sense which thickness of Elevation Shim 110 provides the best "feeling" of proper support.

As an example, if Person 100 determines a 2 mm Elevation Shim 110 placed under the right foot provides the best "feeling", or provides the most "relief", they would order a standard thickness orthotic for their foot condition for their left foot, and a 2 mm thicker orthotic for their foot condition for their right foot. Floor 120 is illustrated as the floor of a building that is directly supporting Person 100's right foot, and supporting Elevation Shim 110 directly, which is in turn supporting Person 100's left foot and making up the difference in leg length.

Figure 4:
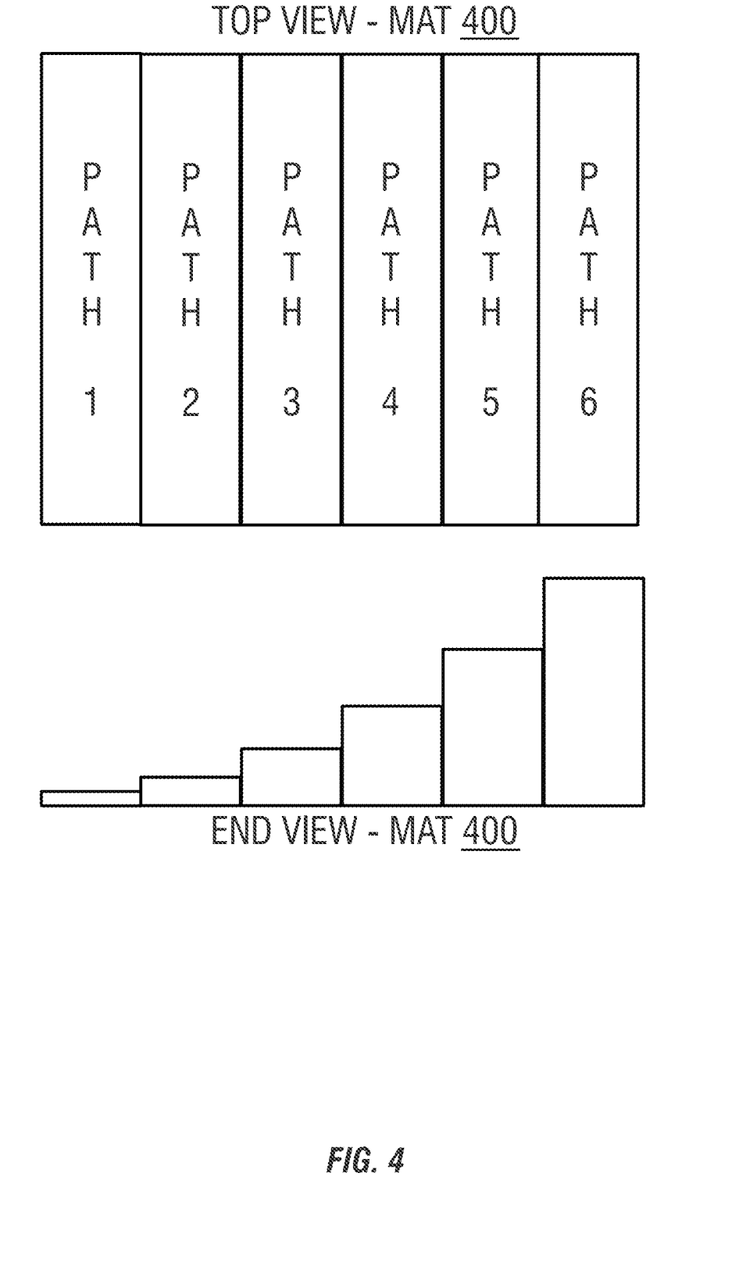
FIG. 4 is an illustration of a mat used in conjunction with the method of the present invention.

Alternatively, the present invention can be implemented using the method described as follows:

The various thicknesses of Elevation Shim 110s needed to measure the potential inequality of leg length in Person 100 can be implemented as a Mat 400, as shown in FIG. 4, with various parallel Elevation Shims 110 built integrally into the Mat 400, as shown in FIG. 4. The following chart is an example of the thicknesses of various parallel Elevation Shim 110 paths for Mat 400 as illustrated in FIG. 4:

CHART 1

| ELEVATION SHIM PARALLEL PATH NUMBER (From One Side Of Mat (Not Shown) To Other Side Of Mat (Not Shown)) | ELEVATION SHIM 110 PATH THICKNESS AS SHOWN IN END VIEW OF FIG. 4 (mm) | DIFFERENCE IN THICKNESS FROM PARALLEL PATH TO PARALELL PATH (mm) |
| --- | --- | --- |
| 1 | 1 | |
| 2 | 2 | Path 1 To Path 2 - 1 mm Difference |
| 3 | 4 | Path 2 To Path 3 - 2 mm Difference |
| 4 | 7 | Path 3 To Path 4 - 3 mm Difference |
| 5 | 11 | Path 4 To Path 4 - 4 mm Difference |
| 6 | 16 | Path 5 To Path 6 - 5 mm Difference |

Person 100 would walk back and forth on Mat 400 as illustrated in FIG. 4 with each foot on a different parallel path, and all the various combinations of neighboring parallel paths of Mat 400 as illustrated in FIG. 4, record their subjective results, and determine which difference in elevation between the various parallel path "feels" the best as applied to either their right or left foot.

Alternatively, Mat 400 can be approximately 12" to 14" long, and a Person 100 could have one at their residence, and stand instead of walk to determine which difference in thickness from parallel path to parallel path best fits a variety of different thickness orthotics they might own to compensate for different leg lengths on different days, which may be due to muscles that are more or less contracted on any particular day, or joints which may be in a different alignment due to a chiropractic adjustment, etc. Person 100 would stand with each foot on a different parallel path, and all the various combinations of neighboring parallel paths of Mat 400 as illustrated in FIG. 4, record their subjective results, and determine which difference in elevation between the various parallel path "feels" the best as applied to either their right or left foot.

Figure 2:
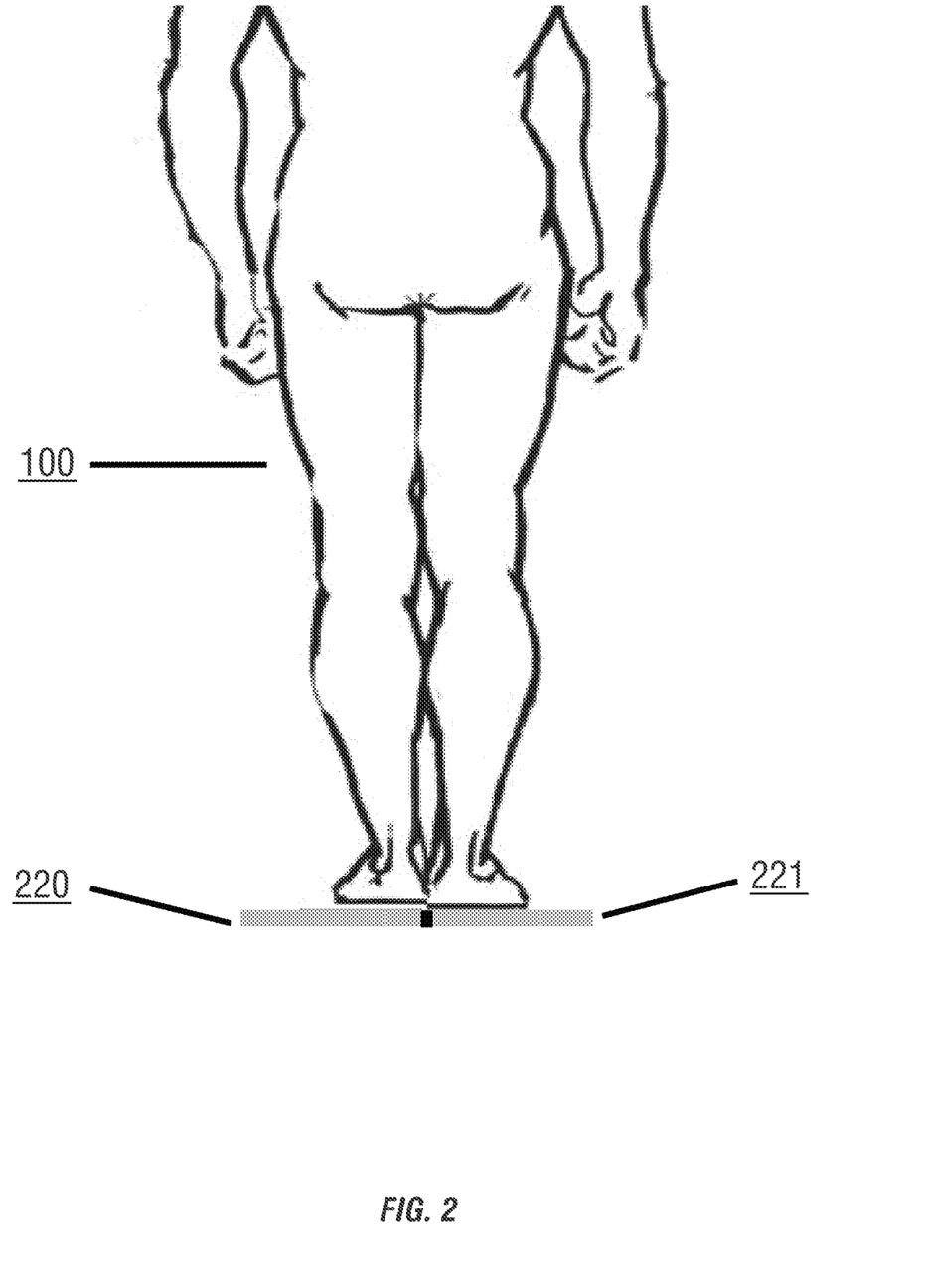
FIG. 2 is an illustration of an alternative embodiment of the present invention.

FIG. 2 is an alternative illustration of a more sophisticated embodiment of the present invention. The element of various thicknesses of Elevation Shim 110 needed to measure the potential inequality of leg length in Person 100 can be implemented without any Elevation Shim 110s. Each section of Split Floor 220, 221 would be raised and lowered continuously using hydraulic cylinder, or electrical cylinder, etc., throughout a range of motion, or to predetermined stops throughout a range of motion in order for Person 100 to assess what "feels" the best in conjunction with the measurements made by a kiosk, or a pair of split, integrated scales with the measurements interpreted by a competent professional such as a doctor, chiropractor, or trained specialist. As the Split Floor 220, 221 is moving throughout its range of motion, Person 100 could be enabled to press a button and record when they "feel" the best at a particular piston stop.

As Split Floor 220, 221 moves through its various stops, it is also designed to return to various stop positions after the initial measurements are made and determine which "feels" better, stop 2 or stop 3, as an example. This is much like the procedure an ophthalmologist, or optometrist does when measuring a person's eyesight, and is fitting them for glasses or contact lenses, "Which is better, A or B?".

As an example, alternatively a orthotic kiosk, such as the Dr. Scholl Orthotic Kiosk could be re-designed to measure and assess the difference in thicknesses needed for either the left or right orthotic to compensate for differences in leg length, in addition to performing the aforementioned measurements designed to choose an orthotic that corrects for foot related problems. These measurements could be done in conjunction with Machine Vision technology, as a sophisticated aid to help measure the relative alignment and height of the left and right hips, left and right knees, left and right ankles, left and right shoulders, left and right eyes, etc. of Person 100. The machine vision technology (not shown) could be used to measure the height of a person as they stand alternatively on each leg independently, as it also measures the position of the knees, hips, shoulders, eyes, etc., as a means to help determine which leg is shorter, or longer, and be used in making an informed judgment based on a variety of measurements, including the all important amount of weight that a person with unequal leg lengths exerts on two independent, integrated scales, The following chart is an example of an orthotic kiosk with built-in piston stops that raise and lower the left and right sections of Split Floor 220, 221 mounted integrally in an orthotic kiosk:

CHART 2

| ORTHOTIC KIOSK SPLIT FLOOR PISTON STOP NUMBER (For Either Left Or Right Moveable Floor Sections Of Orthotic Kiosk) | DIFFERENCE IN FLOOR HEIGHT FROM NEUTRAL POSITION (For Either Left Or Right Moveable Floor Sections Of Orthotic Kiosk) (mm) | RELATES TO AN ELEVATION SHIM THICKNESS OF: (mm) |
|---|---|---|
| 1 | 1 | 1 |
| 2 | 2 | 2 |
| 3 | 3 | 3 |
| 4 | 4 | 4 |
| 5 | 5 | 5 |

Person 100 is illustrated with unequal length legs. The left leg is illustrated as shorter than the right leg.

The Piston Stops in Split Floor 220, 221 which act in the place of Elevation Shims 110 are used to measure, and make up the difference in Person 100's leg length. As the Piston Stops run up and down through a calculated number of positions, constant pressure sensor readouts are taken, which optionally can be made in conjunction with machine vision technology gathering data on the position and angle of the ankles, lower legs, knees, upper legs, hips, shoulders, eyes, etc. The sensor pressure data can be correlated with any optional machine vision data in order to determine the correct orthotic to even foot pressures, as well as the correct difference in thickness of orthotics to compensate for unequal leg lengths. The piston stop positions would relate to one of various thicknesses that could be made available at an orthotic kiosk (such as the Dr. Scholls Orthotic Kiosk illustrated previously), at a Podiatrist's Office, at an Orthotics Store, at a Chiropractor's office, etc.

Figure 5:
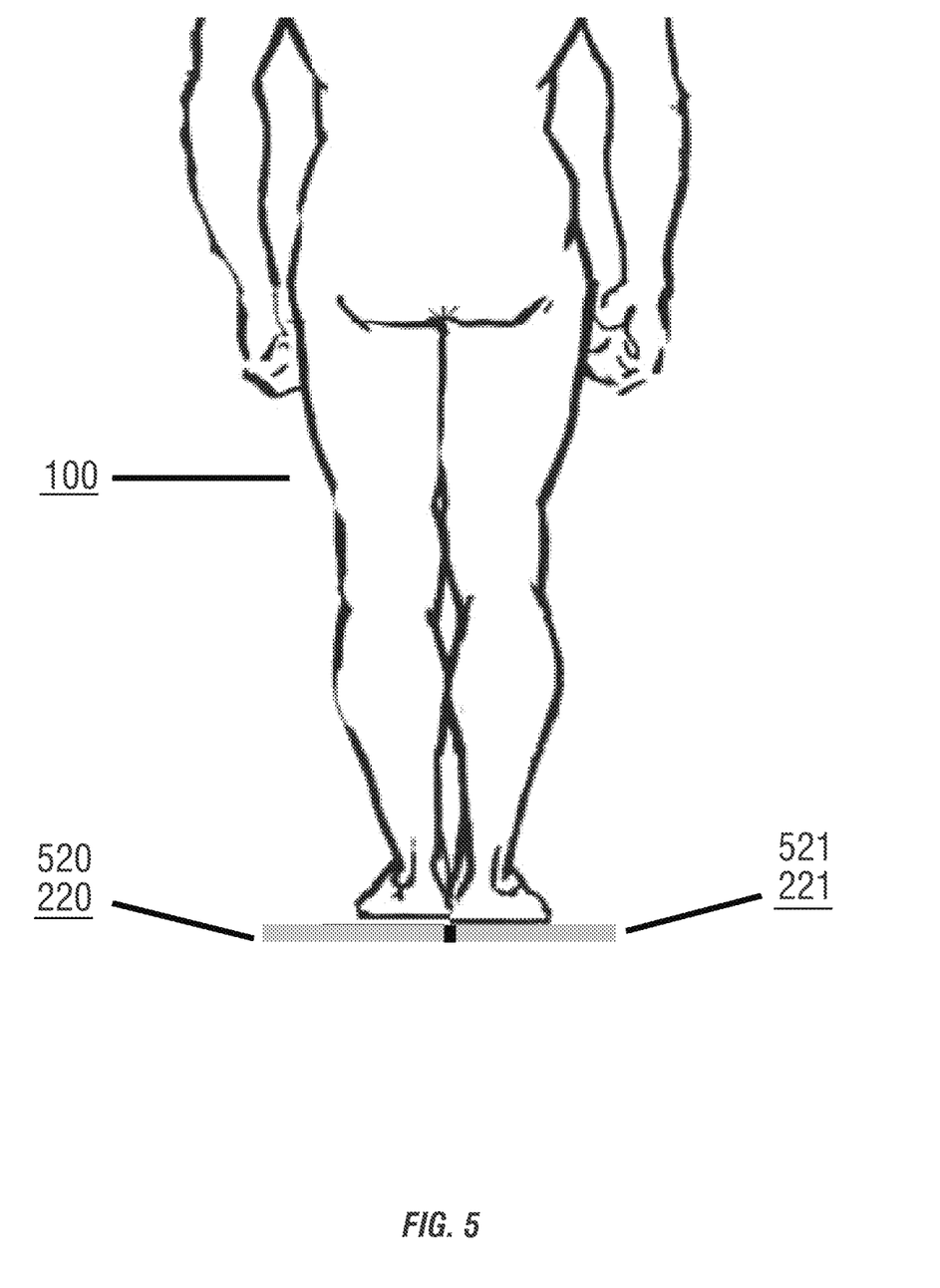
FIG. 5 is an illustration of an alternative embodiment of the present invention.

FIG. 5 is an illustration of an alternative embodiment of the present invention. In this embodiment, the Split Floor 220, 221 as illustrated in FIG. 2 as the floor of an orthotic kiosk, have been replaced by a Split Floor 220, 221 that also includes a pair of high-sample rate scales 520, 521 that directly supporting Person 100's left and right feet independently, which is designed to measure and assess which of Person 100's legs is short or longer than the other, if either.

In FIG. 2, Person 100 is standing on Split Floor 220, 221 which are both located at the same elevation, which include an integrated pair of high-sample rate scales 520, 521, which may be built into an orthotic kiosk, or alternatively implemented as a pair of self-contained integrated scales that may optionally include pressure sensors, but are high-sample rate scales 520, 521 that are integrated, and designed to measure the weight bearing down of the left and right foot of Person 100 individually. The high-sample rate scales 520, 521 that are integrated, will record the weight (in lbs., kgs, etc.) of the amount of weight that is supported by the left and right legs of Person 100 respectively.

As an example, if Person 100 weighs 125.0 lbs., and stands with both feet first on high-sample rate scale 220, and second stands with both feet on high-sample rate scale 520 and also weighs 125.0 lbs., it would be determined that the high-sample rate scales are calibrated at a zero difference relative to one another. The process can optionally be repeated by standing in the reverse direction as well, and both results averaged if there is a slight difference between the readings, and one, or the other scale could be zeroed out relative to the other scale.

Next, if Person 100 stands with one leg on high-sample rate scale 520, and with their other leg on high-sample rate scale 521, which are both integrated, the weights recorded for their left and right legs would be 62.5 lbs. if their legs are of equal length. If Person 100 who is standing with one leg on high-sample rate floor scale 520, and high-sample rate floor scale 521 are different by more than a few pounds, it could be assumed, and eventually determined, that their legs are likely of an unequal length, which would require different thickness orthotics for each leg.

As an example, high-sample rate scale 520 recorded a weight of 75.0 lbs., and high-sample rate scale 521 recorded a weight of 50.0 lbs., for a combined weight of 125.0 lbs. It would be determined that Person 100s leg that recorded a higher weight on high-sample rate scale 520 is likely shorter. This potential difference in leg length could be correlated with machine vision technology readings of the position and alignment of the ankles, knees, hips, shoulders, and eyes. This difference in weight readings on the pair of high-sample rate scales 520, 521, which could be a separate machine, or integrated into an orthotic kiosk, would likely be due to Person 100s center of gravity not bearing down through each leg equally Following is a chart that illustrates the raw data recorded by a high-sample rate floor scale that is sampling every ¹/₁₀th second as Person 100 stands on the pair of high-sample rate scales.

CHART 3

Raw Data Recorded By High-Sample Rate Scale (220, 221)

| Time (Seconds) | Weight Of Left Leg Of 125.0 Lb Person 100 Recorded On High-Sample Rate Scale 520 (Lbs) | Weight Of Right Leg Of 125.0 Lb Person 100 Recorded On High-Sample Rate Scale 521 (Lbs) |
| --- | --- | --- |
| 0.1 | 0.0 | 0.0 |
| 0.2 | 47.0 | 25.0 |
| 0.3 | 59.2 | 38.4 |
| 0.4 | 74.0 | 51.0 |
| 0.5 | 74.2 | 50.8 |
| 0.6 | 75.0 | 50.0 |
| 0.7 | 75.2 | 49.2 |
| 0.8 | 75.4 | 49.6 |
| 0.9 | 74.2 | 50.8 |
| 1.0 | 74.8 | 50.2 |
| 1.1 | 75.2 | 49.8 |
| 1.2 | 73.6 | 51.4 |
| 1.3 | 75.8 | 49.2 |
| 1.4 | 75.0 | 50.0 |
| 1.5 | 43.0 | 37.0 |
| 1.6 | 28.8 | 0.4 |
| 1.7 | 0.2 | 0.3 |
| 1.8 | 0.1 | 0.4 |
| 1.9 | 0.3 | 0.3 |
| 2.0 | 0.0 | 0.0 |

The raw data collected by the pair of high-sample rate scale 520, 521 during the measurements recorded in Chart 3 by programmed logic in a processor operating in conjunction with high-sample rate scale 520, 521 could be interpreted as follows in Chart 4:

CHART 4

0.0 to 0.1 seconds - no weight on scales (scales zeroed relative to one another) (average non-tare readings = 0.0 lbs)
0.2 to 0.3 seconds - Person 100 steps on scales
(data has no meaning, and is discarded from any calculations)
0.4 to 1.4 seconds - Person 100 is standing as still as possible on scales
(average weigh recorded on scale 220 is 74.76 lbs,
and the average weight recorded on scale 221 is 50.18 lbs)
1.5 to 1.6 seconds - Person 100 is getting off scales
(data has no meaning, and is discarded from any calculations)
1.7 to 2.0 seconds - no weight on the scales, scales are zeroing out
(average non-tare weight readings return to 0.0, no adjustments need to be made in any subsequent calculations)

Figure 3:
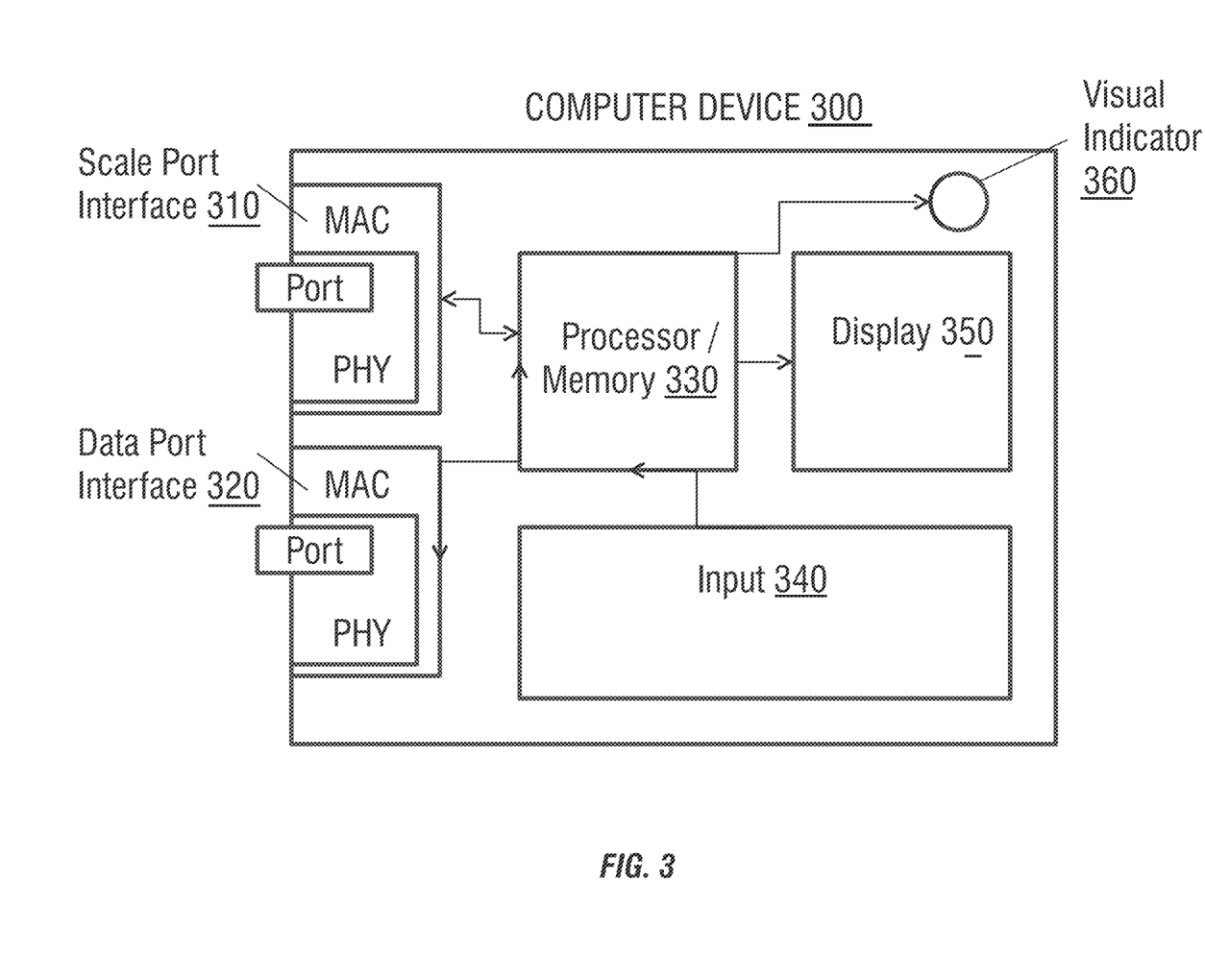
FIG. 3 is an illustration of a compute device used in conjunction with the present invention.

The Split Floor 220, 221 could then be unlocked, and raise up and down throughout their range of motion to determine at what points the integrated high-sample rate scales 520, 521 read within a few tenths of a pound of each other, at which point the compute device illustrated in FIG. 3 would use to determine the difference in shims required for the orthotics needed for person 100.

The high-sample rate scales 520, 521, which are integrated, include a compute device 300 (not shown), that records readings from the high-sample rate scales 520. 521 to be capable of inputting Person 100's identity, as well as a method of storing data, a method of transmitting and receiving data, various ports to connect other devices, and a screen for communicating information with a Person 100, and a doctor, chiropractor, or other trained professional.

FIG. 3 is a block diagram of a compute device (300) which can be attached to, or integrated into, a high-sample rate scales 520, 521 as illustrated in FIG. 5, which may be a pair of high-sample rate scales 520, 521, which may be independent, or alternatively integrated into the floor of an orthotic kiosk.

Compute device (300) is comprised of the following elements, a scale port interface (310), which includes a PHY and MAC; a data port interface (320), which includes a PHY and MAC; a processor with memory (330); an input (340); and outputs including: a display (350), and visual indicator (360).

The present invention includes a scale port interface (310), which includes a PHY and MAC, is provided for interfacing with scale high-sample rate scale 520,521 as illustrated in FIG. 2.

Scale port interface (310) can be a wired or wireless connection.

Examples of a wired connection include, but are not limited to, RS-232, Serial RS-232 max, RS-422-B, RS-423-B, RS-449, RS-485, RS-530, RS 561, RS-562, RS-612, RS-613, USB Low Speed, Parallel (Centronics), Serial RS-422 max, USB Full Speed, FireWire (IEEE 1394) 100, Fast Wide SCSI 2, FireWire (IEEE 1394) 200, FireWire (IEEE 1394) 400, USB Hi-Speed, FireWire (IEEE 1394b), etc.

Examples of a wireless connection include, but are not limited to, IrDA-Control, 802.15.4 (2.4 GHz), Bluetooth 1.1, 802.11 legacy, Bluetooth 2, RONJA free source optical wireless, 802.11b DSSS, 802.11b+ non-standard DSSS, 802.11a, 802.11g DSSS, 802.11n, 802.16 (WiBro) and 802.16 (Hiperman), etc. Other examples of a wireless connection include, but are not limited to cell phone standards such as, but not limited to, GSM, UMTS, IS-95, CDMA 2000, etc.

The present invention includes a scale port interface 320, which includes a PHY and MAC, is provided for interfacing with a Person 100 (not shown) and/or a doctor, chiropractor, or trained professional (not shown), or another person, or a remotely located server, web-based application, business information system, database, software application, cell phone application, etc. Data port interface (320) can be a wired or wireless connection.

Examples of a wired connection include, but are not limited to, RS-232, Serial RS-232 max, RS-422-B, RS-423-B, RS-449, RS-485, RS-530, RS 561, RS-562, RS-612, RS-613, USB Low Speed, Parallel (Centronics), Serial RS-422 max, USB Full Speed, FireWire (IEEE 1394) 100, Fast Wide SCSI 2, FireWire (IEEE 1394) 200, FireWire (IEEE 1394) 400, USB Hi-Speed, FireWire (IEEE 1394b), magnetic stripe card reader, bar code scanner, etc.

Examples of a wireless connection include, but are not limited to, IrDA-Control, 802.15.4 (2.4 GHz), Bluetooth 1.1, 802.11 legacy, Bluetooth 2, RONJA free source optical wireless, 802.11b DSSS, 802.11b+ non-standard DSSS, 802.11a, 802.11g DSSS, 802.11n, 802.16 (WiBro) and 802.16 (Hiperman), GSM CSD, HSCSD, GPRS, UMTS, CDMA, and TDMA, RFID, etc.

The present invention may include a processor with memory (330). The memory may be on-board processor memory, or separate memory in compute device (300). Processor with memory (330) may be a device such as, but not limited to, a field programmable gate array (FPGA), an ASIC, etc.

The present invention includes an input (340). Input 340 may be a device such as, but not limited to, a keyboard, a touch screen, etc.

The present invention includes a display 350. Display 350 may be a device such as, but not limited to, a LCD (Liquid Crystal Display), a TFT (Thin Film Transistor), an OLED (Organic Light Emitting Diode), CRT (Cathode Ray Tube), etc. Display 350 can be used to display messages related to the Person 100, or doctor, chiropractor, trained professional, etc., regarding the measurements taken, whether a re-take is needed, advertising, inspirational messages, etc.

The present invention includes a visual indicator 360. Visual indicator 360 may be a device such as, but not limited to, an LED (Light Emitting Diode). Only one is shown for clarity, but other visual indicators 360 may be included.

In addition, to the various methods outlined in FIG. 1, FIG. 2, and FIG. 5 for helping person 100 determine which thickness of orthotics to purchase to correct for their unequal length legs, they may use the following method to help determine which leg is shorter, and an approximate difference in leg length. Any person 100 with unequal length legs will tend to stand on their shorter leg in a vertical alignment with the rest of their body, and with their long length leg off the side. Their legs form a right triangle, which can be analyzed using the Pythagorean theorem or Pythagoras' theorem is a relation in Euclidean geometry among the three sides of a right triangle (right-angled triangle). In terms of areas, it states: In any right-angled triangle, the area of the square whose side is the hypotenuse (the side opposite the right angle) is equal to the sum of the areas of the squares whose sides are the two legs (the two sides that meet at a right angle). The theorem can be written as an equation relating the lengths of the sides a, b and c, often called the Pythagorean equation:

$$a^2+b^2=c^2$$

where c represents the length of the hypotenuse, and a and b represent the lengths of the other two sides.

Applying the Pythagorean equation to the problem of unequal length legs on any person 100, a represents the distance between the center of the back of the heels on the left and right legs, b represents the distance from the floor to the crotch for the short leg (the leg in vertical alignment with the rest of the body), and c represents the unknown leg length of the long leg (the leg that is oriented off to the side of person 100's body).

Solving for c then, the following equation can be used to determine the leg length of the long leg:

$$c=(a^2+b^2)^{1/2}$$

Once c is known, the difference in leg length is calculated as follows:

$$c-b=\text{Difference In Leg Length}$$

The optionally calculated Difference In Leg Length will be a good approximation, and a quick quality check of the Difference in Leg Length determined in the steps and methods associated with FIG. 1, FIG. 2, FIG. 5, as was illustrated in FIG. 4.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to a particular embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements.

What has been described herein is a system, method, and apparatus for providing a quick, accurate set of measurements to determine the difference, if any, of a person's left and right leg lengths, in order to determine the thickness of an insert for the left and/or right shoes in order to provide correction and alignment of a person's skeletal frame, and it should be apparent to those skilled in the art that certain advantages of the present invention have been achieved. It should also be appreciated that various modifications, adaptations, and alternatives may be made. It is of course not possible to describe every conceivable combination of components for purposes of describing the present invention. All such possible modifications are to be included within the spirit and scope of the present invention which is to be limited only by the following claims.

What is claimed is:

1. A method for providing a measurement of the difference, if any, of left and right leg lengths of a person, in order to determine a thickness of an orthotic insert for a left shoe and a right shoe, the method comprising the steps of:

providing an apparatus with a left surface and a right surface, the left surface associated with a first scale and the right surface associated with a second scale and wherein the apparatus is configured to independently lift and lower the left surface and the right surface to predetermined stops while the person is standing on the left surface and the right surface and to sense pressure with pressure sensors comprising a first pressure sensor associated with the left surface and a second pressure sensor associated with the right surface, the apparatus further comprising a processor operatively connected to the first scale and the second scale and the pressure sensors;

weighing a person's weight bearing through both a left foot with the first scale, and simultaneously and independently weighing the person's weight bearing through a right foot with the second scale;

changing a height of the left surface or the right surface from a neutral position between the person's left and right feet during said simultaneous and independent weight measurements by lifting or lowering the left surface and/or the right surface to the predetermined stops, such that the weight associated with the first scale and the weight associated with the second scale is an indication of said person's center of gravity bearing through the left and right legs;

sensing pressure using the first pressure sensor of the first scale and the second pressure sensor of the second scale to provide pressure data; and using the processor to determine the thickness of the orthotic insert for the left shoe and the right shoe to even foot pressures for compensating for unequal leg lengths using the sensed pressure and a height difference between the left surface and the right surface.

2. The method of claim 1 wherein the apparatus further comprises a display operatively connected to the processor.

3. A method for providing a measurement of the difference, if any, of left and right leg lengths of a person, in order to determine a thickness of an orthotic insert for a left shoe and a right shoe, the method comprising the steps of:

providing an apparatus with a left surface and a right surface, the left surface associated with a first scale and the right surface associated with a second scale and wherein the apparatus is configured to independently lift and lower the left surface and the right surface to predetermined stops while the person is standing on the left surface and the right surface and to sense pressure with pressure sensors comprising a first pressure sensor associated with the left surface and a second pressure sensor associated with the right surface, the apparatus further comprising a processor operatively connected to the first scale and the second scale and the pressure sensors;

weighing a person's weight bearing through both a left foot with the first scale, and simultaneously and independently weighing the person's weight bearing through a right foot with the second scale;

changing a height of the left surface or the right surface from a neutral position between the person's left and right feet during said simultaneous and independent weight measurements by lifting or lowering the left surface and/or the right surface to the predetermined stops;

sensing pressure using the first pressure sensor of the first scale and the second pressure sensor of the second scale to provide pressure data; and using the processor to determine the thickness of the orthotic insert for the left shoe and the right shoe to even foot pressures by for compensating for unequal leg lengths using the sensed pressure and a height difference between the left surface and the right surface.

* * * * *